United States Patent
Collins et al.

(10) Patent No.: US 10,377,643 B1
(45) Date of Patent: Aug. 13, 2019

(54) ULTRAVIOLET DISINFECTION SYSTEM

(71) Applicant: RayVio Corporation, Hayward, CA (US)

(72) Inventors: Douglas A. Collins, Hayward, CA (US); Yitao Liao, Redwood City, CA (US); Robert S. West, Pleasanton, CA (US)

(73) Assignee: RayVio Corporation, Hayward, CA (US)

( * ) Notice: Subject to any disclaimer, the term of this patent is extended or adjusted under 35 U.S.C. 154(b) by 0 days.

(21) Appl. No.: 15/485,177

(22) Filed: Apr. 11, 2017

Related U.S. Application Data

(63) Continuation of application No. 15/367,009, filed on Dec. 1, 2016, which is a continuation of application No. 14/733,494, filed on Jun. 8, 2015, now Pat. No. 9,540,252.

(51) Int. Cl.
| | | |
|---|---|---|
| *C02F 1/32* | (2006.01) | |
| *A61L 2/10* | (2006.01) | |
| *C02F 1/72* | (2006.01) | |
| *C02F 1/00* | (2006.01) | |

(52) U.S. Cl.
CPC .............. *C02F 1/325* (2013.01); *A61L 2/10* (2013.01); *C02F 1/008* (2013.01); *C02F 1/725* (2013.01); *C02F 2201/3222* (2013.01); *C02F 2201/3228* (2013.01); *C02F 2305/10* (2013.01)

(58) Field of Classification Search
CPC ............. C02F 1/325; C02F 2201/3222; C02F 2201/3228; A61L 2/10
See application file for complete search history.

(56) References Cited

U.S. PATENT DOCUMENTS

| | | | |
|---|---|---|---|
| 5,861,123 A | * | 1/1999 | Schifftner ................ A61L 2/10 250/432 R |
| 5,919,422 A | | 7/1999 | Yamanaka et al. |
| 6,500,387 B1 | | 12/2002 | Bigelow |
| 6,773,608 B1 | * | 8/2004 | Hallett ................ A61L 2/0047 210/150 |
| 8,422,311 B1 | * | 4/2013 | Roberts ................ G11C 16/18 365/185.02 |
| 9,617,171 B2 | | 4/2017 | Rajagopalan et al. |
| 2002/0113022 A1 | | 8/2002 | Gadgil et al. |
| 2003/0170151 A1 | | 9/2003 | Hunter et al. |
| 2010/0237254 A1 | | 9/2010 | Mason et al. |
| 2010/0314551 A1 | * | 12/2010 | Bettles ..................... C02F 1/32 250/432 R |
| 2011/0267805 A1 | | 11/2011 | Hua et al. |
| 2011/0309032 A1 | | 12/2011 | Makl |
| 2012/0132947 A1 | | 5/2012 | Krauter |
| 2014/0263091 A1 | | 9/2014 | Carter, III et al. |
| 2015/0008167 A1 | | 1/2015 | Shturm |
| 2015/0114912 A1 | | 4/2015 | Taghipour |

(Continued)

*Primary Examiner* — Eliza W Osenbaugh-Stewart
(74) *Attorney, Agent, or Firm* — Patent Law Group LLP; Brian D. Ogonowsky

(57) ABSTRACT

Embodiments of the invention include an elongate chamber. A UV source includes a semiconductor device, the semiconductor device including an active layer disposed between an n-type region and a p-type region. The active layer emits radiation having a peak wavelength in a UV range. The semiconductor device is positioned on a wall of the elongate chamber. An inner surface of the elongate chamber is reflective.

17 Claims, 4 Drawing Sheets

(56) References Cited

U.S. PATENT DOCUMENTS

| | | | |
|---|---|---|---|
| 2015/0129776 A1 | 5/2015 | Boodaghians et al. | |
| 2015/0129777 A1* | 5/2015 | Nikamoto | C02F 1/325 250/435 |
| 2015/0144575 A1* | 5/2015 | Hawkins, II | A61L 2/10 210/748.11 |
| 2015/0174528 A1 | 6/2015 | Son et al. | |
| 2015/0287894 A1* | 10/2015 | Toita | H01L 33/58 257/98 |
| 2015/0314024 A1* | 11/2015 | Khan | C02F 1/325 250/435 |
| 2015/0338336 A1 | 11/2015 | Dobrinsky | |
| 2015/0344329 A1 | 12/2015 | Smetona | |
| 2016/0107904 A1* | 4/2016 | Rajagopalan | C02F 1/325 250/432 R |
| 2017/0166458 A1 | 6/2017 | Rimbault et al. | |

\* cited by examiner

ULTRAVIOLET DISINFECTION SYSTEM

CROSS-REFERENCE TO RELATED APPLICATIONS

The present application is a continuation of U.S. patent application Ser. No. 15/367,009, filed Dec. 1, 2016, titled "ULTRAVIOLET DISINFECTION SYSTEM", which is a continuation of U.S. patent application Ser. No. 14/733,494 filed on Jun. 8, 2015, now U.S. Pat. No. 9,540,252, which issued Jan. 10, 2017. U.S. patent application Ser. No. 14/733,494, and U.S. Pat. No. 9,540,252 are incorporated herein.

BACKGROUND

Description of Related Art

The bandgap of III-nitride materials, including (Al, Ga, In)—N and their alloys, extends from the very narrow gap of InN (0.7 eV) to the very wide gap of AlN (6.2 eV), making III-nitride materials highly suitable for optoelectronic applications such as light emitting diodes (LEDs), laser diodes, optical modulators, and detectors over a wide spectral range extending from the near infrared to the deep ultraviolet. Visible light LEDs and lasers can be obtained using InGaN in the active layers, while ultraviolet (UV) LEDs and lasers require the larger bandgap of AlGaN.

UV LEDs with emission wavelengths in the range of 230-350 nm are expected to find a wide range of applications, most of which are based on the interaction between UV radiation and biological material. Typical applications include surface sterilization, water purification, medical devices and biochemistry, light sources for ultra-high density optical recording, white lighting, fluorescence analysis, sensing, and zero-emission automobiles.

UV radiation has disinfection properties that inactivate bacteria, viruses, and other microorganisms. A low-pressure mercury lamp may produce UV radiation in the range of 254 nm. Since most microorganisms are affected by radiation around 260 nm, UV radiation is in the appropriate range for germicidal activity. FIG. 1 illustrates a known UV treatment device. A cylindrical chamber 110 houses a UV bulb 112 along a central axis of the chamber 110. The bulb may be encased in a quartz sleeve. UV radiation 114 is emitted from the bulb 112. Untreated water enters the chamber at inlet 116, and flows toward outlet 118, where treated water may be removed from the chamber. A flow control device 120 may prevent the water from passing too quickly past the bulb, assuring appropriate radiation contact time with the flowing water. The chamber is stainless steel.

DETAILED DESCRIPTION

Though the devices described herein are III-nitride devices, devices formed from other materials such as other III-V materials, II-VI materials, Si are within the scope of embodiments of the invention. The devices described herein may be configured to emit UV A (peak wavelength between 340 and 400 nm), UV B (peak wavelength between 290 and 340 nm), or UV C (peak wavelength between 210 and 290 nm) radiation.

In embodiments of the invention, one or more UVLEDs are used in a disinfection device, suitable for disinfecting a fluid, such as water, air, or any other suitable material.

Figure 2:
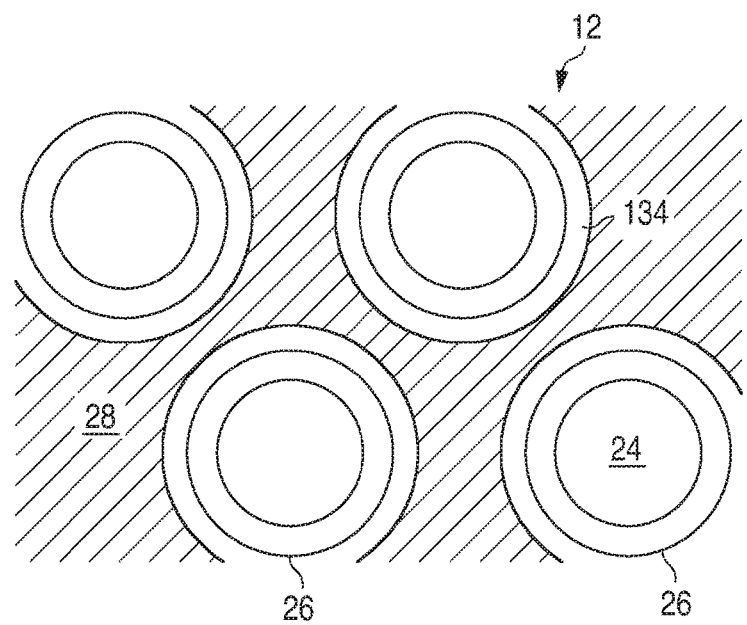
FIG. 2 is a plan view of multiple pixels in a flip chip UV-emitting device (UVLED).
Figure 3:
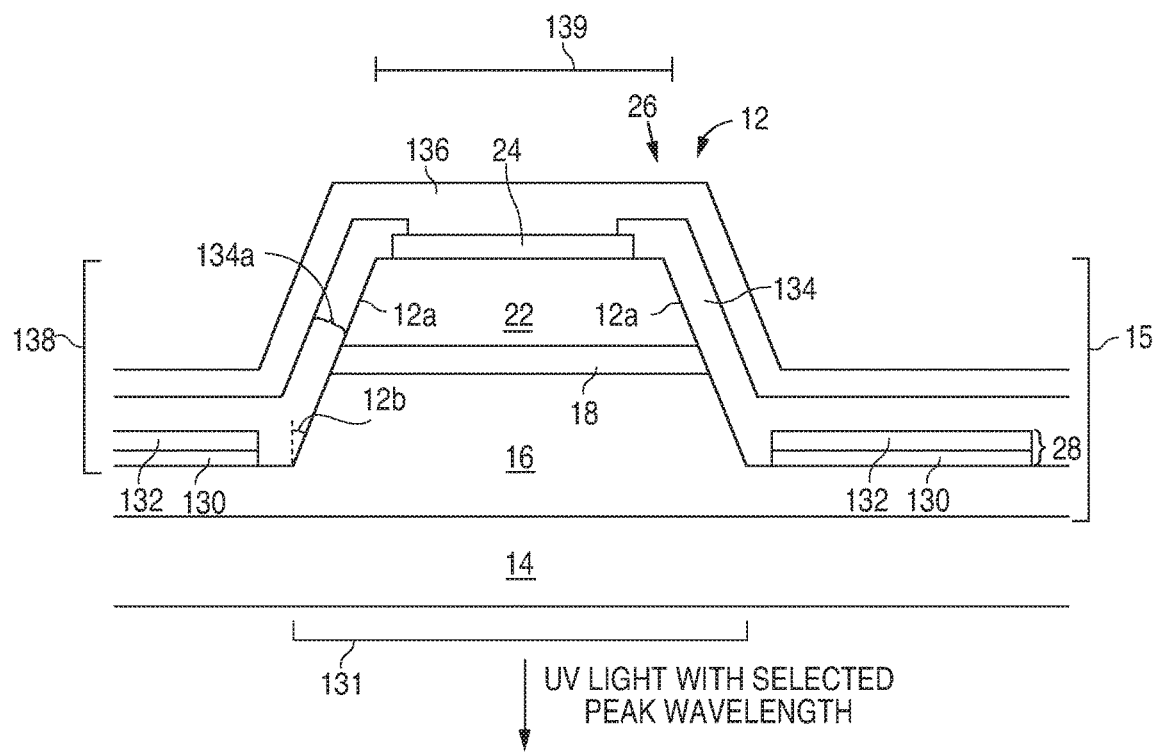
FIG. 3 is a cross sectional view of one pixel in the UVLED of FIG. 2.

Commercially available UVA, UVB, and UVC LEDs may be used in the various embodiments. FIGS. 2 and 3 are examples of the assignee's own UVB and UVC LEDs that may be used. FIG. 2 is a top down view of a portion of an array of UVLED pixels 12, and FIG. 3 is a bisected cross-section of a single UVLED pixel 12. Any suitable UVLED may be used and embodiments of the invention are not limited to the device of FIGS. 2 and 3.

The UVLEDs are typically III-nitride, and commonly GaN, AlGaN, and InGaN. The array of UV emitting pixels 12 is formed on a single substrate 14, such as a transparent sapphire substrate. Other substrates are possible. Although the example shows the pixels 12 being round, they may have any shape, such as square. The light escapes through the transparent substrate, as shown in FIG. 3. The pixels 12 may each be flip-chips, where the anode and cathode electrodes face the mount (described below).

All semiconductor layers are epitaxially grown over the substrate 14. An AlN or other suitable buffer layer (not shown) is grown, followed by an n-type region 16. The n-type region 16 may include multiple layers of different compositions, dopant concentrations, and thicknesses. The n-type region 16 may include at least one $Al_aGa_{1-a}N$ film doped n-type with Si, Ge and/or other suitable n-type dopants. The n-type region 16 may have a thickness from about 100 nm to about 10 microns and is grown directly on the buffer layer(s). The doping level of Si in the n-type region 16 may range from $1\times10^{16}$ cm$^{-3}$ to $1\times10^{21}$ cm$^{-3}$. Depending on the intended emission wavelength, the AlN mole fraction "a" in the formula may vary from 0% for devices emitting at 360 nm to 100% for devices designed to emit at 200 nm.

An active region 18 is grown over the n-type region 16. The active region 18 may include either a single quantum well or multiple quantum wells (MQWs) separated by barrier layers. The quantum well and barrier layers contain $Al_xGa_{1-x}N/Al_yGa_{1-y}N$, wherein $0<x<y<1$, x represents the AlN mole fraction of a quantum well layer, and y represents the AlN mole fraction of a barrier layer. The peak wavelength emitted by a UV LED is generally dependent upon the relative content of Al in the AlGaN quantum well active layer.

A p-type region 22 is grown over the active region 18. Like the n-type region 16, the p-type region 22 may include multiple layers of different compositions, dopant concentrations, and thicknesses. The p-type region 22 includes one or more p-type doped (e.g. Mg-doped) AlGaN layers. The AlN mole fraction can range from 0 to 100%, and the thickness of this layer or multilayer can range from about 2 nm to about 100 nm (single layer) or to about 500 nm (multilayer). A multilayer used in this region can improve lateral conductivity. The Mg doping level may vary from $1 \times 10^{16}$ $cm^{-3}$ to $1 \times 10^{21}$ $cm^{-3}$. A Mg-doped GaN contact layer may be grown last in the p-type region 22.

All or some of the semiconductor layers described above may be grown under excess Ga conditions, as described in more detail in US 2014/0103289, which is incorporated herein by reference.

The semiconductor structure 15 is etched to form trenches between the pixels 12 that reveal a surface of the n-type region 16. The sidewalls 12a of the pixels 12 may be vertical or sloped with an acute angle 12b relative to a normal to a major surface of the growth substrate. The height 138 of each pixel 12 may be between 0.1-5 microns. The widths 131 and 139 at the bottom and top of each pixel 12 may be at least 5 microns. Other dimensions may also be used.

Before or after etching the semiconductor structure 15 to form the trenches, a metal p-contact 24 is deposited and patterned on the top of each pixel 12. The p-contact 24 may include one or more metal layers that form an ohmic contact, and one or more metal layers that form a reflector. One example of a suitable p-contact 24 includes a Ni/Ag/Ti multi-layer contact.

An n-contact 28 is deposited and patterned, such that n-contact 28 is disposed on the substantially flat surface of the n-type region 16 between the pixels 12. The n-contact 28 may include a single or multiple metal layers. The n-contact 28 may include, for example, an ohmic n-contact 130 in direct contact with the n-type region 16, and an n-trace metal layer 132 formed over the ohmic n-contact 130. The ohmic n-contact 130 may be, for example, a V/Al/Ti multi-layer contact. The n-trace metal 132 may be, for example, a Ti/Au/Ti multi-layer contact.

The n-contact 28 and the p-contact 24 are electrically isolated by a dielectric layer 134. Dielectric layer 134 may be any suitable material such as, for example, one or more oxides of silicon, and/or one or more nitrides of silicon, formed by any suitable method. Dielectric layer 134 covers n-contact 28. Openings formed in dielectric layer 134 expose p-contact 24.

A p-trace metal 136 is formed over the top surface of the device, and substantially conformally covers the entire top surface. The p-trace metal 136 electrically connects to the p-contact 24 in the openings formed in dielectric layer 134. The p-trace metal 136 is electrically isolated from n-contact 28 by dielectric layer 134.

Robust metal pads electrically connected to the p-trace metal 136 and n-contact 28 are provided outside of the drawing for connection to power supply terminals. Multiple pixels 12 are included in a single UVLED. The pixels are electrically connected by large area p-trace metal 136 and the large area n-trace metal 132. The number of pixels may be selected based on the application and/or desired radiation output. A single UVLED, which includes multiple pixels, is illustrated in the following figures as UVLED 1.

In some embodiments, substrate 14 is sapphire. Substrate 14 may be, for example, on the order of hundred of microns thick. In a 1 mm square UVLED 1 with a 200 µm thick sapphire substrate, assuming radiation is extracted from the top and sides of the substrate, the top surface accounts for about 55% of the extraction surface, and the sides account for about 45% of the extraction surface of the substrate. Substrate 14 may remain part of the device in some embodiments, and may be removed from the semiconductor structure in some embodiments.

The UVLED may be square, rectangular, or any other suitable shape when viewed from the top surface of substrate 14, when the device is flipped relative to the orientation illustrated in FIG. 3.

Figure 4:
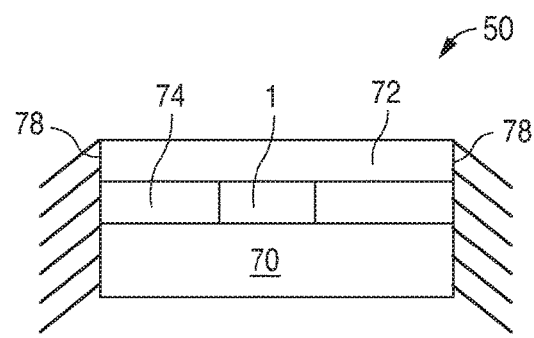
FIG. 4 illustrates a package including a UVLED and a transparent plate.
Figure 5:
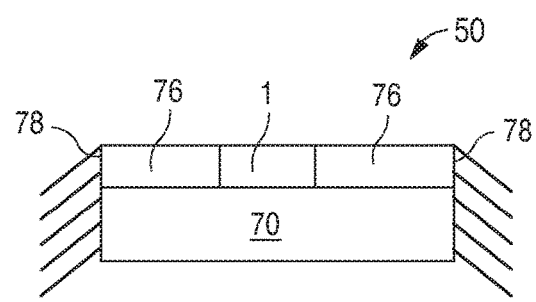
FIG. 5 illustrates a package including a UVLED and a sealing material.
Figure 6:
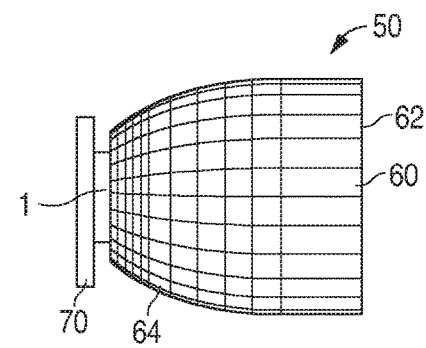
FIG. 6 illustrates a package including a UVLED and an optic.

The UVLED illustrated in FIGS. 2 and 3 may be disposed in a package. Three packages are illustrated in FIGS. 4, 5, and 6. In each package, UVLED 1 is attached to a mount 70. The mount 70 may be, for example, a ceramic mount, a circuit board, a metal-core printed circuit board, a silicon mount, or any other suitable structure. Circuit elements such as driver circuitry for UVLED 1 or any other suitable circuitry may be disposed on or within mount 70. In each of the packages illustrated in FIGS. 4, 5, and 6, more than one UVLED may be attached to mount 70. In each of the disinfection chambers described below, a single UVLED may be used, multiple UVLEDs disposed in a single package may be used, or multiple packages including one or more UVLEDs each may be used, in order to provide UV radiation sufficient for disinfection in the disinfection chamber.

In the package of FIG. 4, UVLED 1 is attached to mount 70. A transparent plate 72 is disposed over UVLED 1. Transparent plate 72 may be quartz or any suitable material. UVLED 1 may be in direct physical contact with transparent plate 72 as illustrated in FIG. 4, in optical contact with transparent plate 72 by, for example, filling the space 74 between mount 70 and transparent plate 72 with an index matching material such as oil or any other suitable material, or spaced apart from transparent plate 72.

In the package of FIG. 5, UVLED 1 is attached to mount 70. UVLED 1 and empty space on mount 70 adjacent to UVLED 1 are covered with a material 76 that seals UVLED 1. Suitable sealing materials are UV-hard, transparent, and protect UVLED 1. Any suitable material, such as glass, may be applied by any suitable technique, such as a sol gel process. Sealing material over the top surface of UVLED 1 may be etched back to reveal the top surface of UVLED 1 (often the top surface of the grown substrate).

In the packages of FIGS. 4 and 5, in some embodiments, sidewalls 78 form a sealed chamber, such that UVLED 1 is isolated and protected from the fluid to be disinfected. For example, if the fluid is a liquid, the mount 70, sidewalls 78, and transparent plate 72 or sealing material 76 form a water-tight compartment in which UVLED 1 is placed. The sidewalls 78 may be walls of the disinfecting chamber, a metal or plastic container, or any other suitable structure.

In the package of FIG. 6, a UVLED 1 is attached to a mount 70, and an optic 60 is attached to the UVLED 1. The optic 60 may be any suitable optic, including for example, a dome lens, a Fresnel lens, the compound parabolic collimator illustrated, or any other suitable lens or optic. The optic 60 illustrated in FIG. 6 may create a radiation pattern that is more collimated than the radiation pattern emitted by the UVLED 1 without the optic 60. In some embodiments, the optic 60 is a compound parabolic collimator. UV radiation encountering curved sidewall 64 is reflected toward outlet surface 62. The optic 60 may be a solid, transparent material, that reflects UV radiation off sidewalls 64 by total internal reflection (TIR), or an open, hollow structure filled with air, with sidewalls that are formed from or coated with reflective material. In the case of an open structure, the outlet surface 62 may be simply an opening. A compound parabolic collimator may be more suited to an application where the UV radiation source is disposed on an end wall of an elongate disinfection chamber. A dome lens may be more suited to an application where the UV radiation source is disposed on a side wall of an elongate disinfection chamber.

Optic 60 may be a truncated inverted pyramid or cone. The outlet surface 62 of optic 60 may be, for example, rotationally symmetric, oval, round, square, rectangular, or any other suitable shape. The shape of the outlet surface 62 of optic 60 may be matched to the shape of the disinfection vessel. The surface of the optic 60 that is optically coupled to the top surface of the UVLED may be only slightly larger than the top surface of the UVLED; no more than 10% larger in some embodiments, no more than 20% larger in some embodiments, and no more than 30% larger in some embodiments. In some embodiments, a lens or other optic is disposed over UVLED 1, between the UVLED 1 and optic 60.

A solid optic 60 is formed from a material that is transparent to UV radiation at wavelengths emitted by UVLED 1, and able to withstand the UV radiation without degrading. For example, in some embodiments, the optic may be formed from a material that transmits at least 85% of UV radiation at 280 nm. The material may degrade no more than 1% after 1000 hrs of exposure to UV radiation at 280 nm. In some embodiments, optic 60 is formed from a material that is moldable, such as, for example, glass, IHU UV transmissive glass available from Isuzu Glass, Inc., and UV-resistant silicone. In some embodiments, optic 60 is formed from a material that may be shaped by, for example, grinding and polishing, such as quartz or sapphire. An optic formed by molding may be less expensive; an optic formed by grinding and polishing may be of better optical quality.

In some embodiments, optic 60 is optically coupled to only the top surface of the UVLED 1, typically a surface of the growth substrate, or a major surface of the semiconductor structure of UVLED 1. In some embodiments, optic 60 may extend over and be optically coupled to the sides of UVLED 1 as well. Optic 60 may extend over the sides of just the growth substrate, or over the sides of both the growth substrate and the semiconductor structure.

As illustrated in FIG. 6, in some embodiments, only the top surface of UVLED 1 is optically coupled to the optic 60. The side surfaces of UVLED 1 are not optically coupled to the optic, such that radiation emitted from the side surfaces is lost. Capturing the radiation from just the top surface increases the etendue of the UVLED/optic system. Increasing the etendue may increase the irradiance of the system and reduce the source size, which may be useful for some applications. The radiation emitted to the side is discarded in these embodiments, though in UV-emitting systems, radiation may preferentially be emitted toward the side surfaces of a UVLED, rather than the top surface of the UVLED, due to polarization within the AlGaN active layer(s).

In embodiments where the optic is a solid material that directs radiation by total internal reflection such as, for example, the optic illustrated in FIG. 6, the optic may have a TIR surface combined with other surfaces that may or may not direct radiation by TIR. For example, the TIR surfaces 64 of the optic illustrated in FIG. 6 may be combined with a domed surface spaced apart from UVLED 1, for example in place of flat output surface 62.

A UVLED 1 with an optic 60 may be used in a disinfection chamber as illustrated in FIG. 6, in either of the packages illustrated in FIG. 4 or 5, or in any other suitable package.

Figure 7:
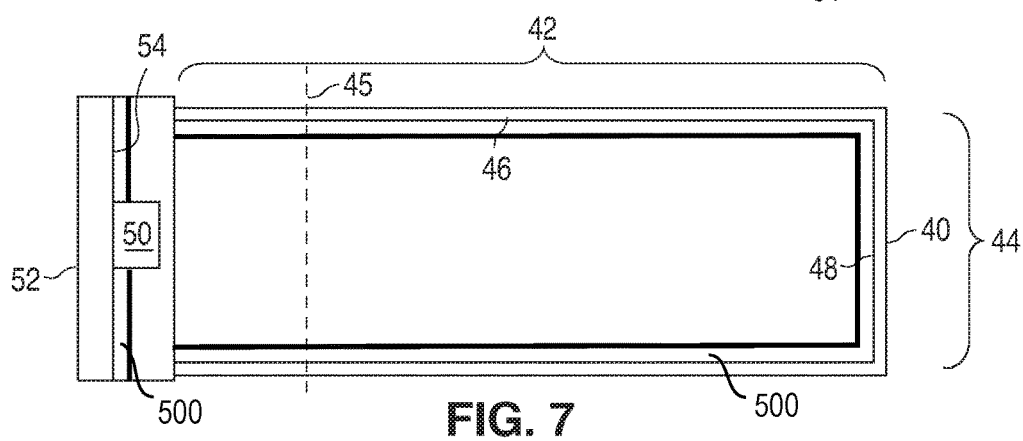
FIG. 7 is a cross sectional view of a batch-process UV disinfection system.

FIG. 7 is a cross sectional view of one embodiment of a disinfection device. The device of FIG. 7 includes a disinfection chamber 40. The disinfection chamber 40 is elongate; length 42 may be, for example, at least five times greater than width 44 in some embodiments, and no more than a hundred times greater than width 44 in some embodiments. The cross section at plane 45 may be circular, square, rectangular, hexagonal, or any other suitable shape.

UV radiation source 50 is disposed along at least one wall of the disinfection chamber. In the embodiment illustrated in FIG. 7, one UV radiation source 50 is disposed at one end of the elongate disinfection chamber 40, on one of the short walls of the disinfection chamber. In each of the disinfection chambers described herein, a single UV radiation source may be positioned on any wall of the disinfection chamber, or in any part of the disinfection chamber, or multiple UV radiation sources may be positioned on the same or multiple walls of the disinfection chamber. In some embodiments, a UV radiation source is positioned on a longer sidewall of the elongate chamber, rather than or in addition to on a shorter end wall of the elongate chamber. In some embodiments, UV radiation sources are positioned on both end walls of the disinfection chamber. In order to achieve a predetermined amount of UV radiation for disinfection at every point in the chamber, the use of two UV radiation sources at either end of the chamber may allow lower power UV devices to be used, as compared with a single UV radiation source positioned at one end, which must produce sufficient UV radiation at the opposite end of the chamber.

In the embodiment illustrated in FIG. 7, UV radiation source 50 may be disposed on what may be considered the top of the disinfection chamber. The surface 54 of the top 52 of the disinfection chamber that faces into the disinfection chamber may be formed from or coated with a UV-reflective material. The surface 48 of the bottom of the disinfection chamber (i.e., the short wall opposite the top) that faces into the disinfection chamber may be formed from or coated with a UV-reflective material. Surfaces 48 and 54 may have the same reflective coating, though this is not required. Examples of suitable reflective coatings for surfaces 48 and 54 include metals, silver, aluminum, Teflon, polytetrafluoroethylene (PTFE), barium sulfate, oxides, oxides of silicon including $SiO_2$, oxides of yttrium, oxides of hafnium, a multilayer stack, a distributed Bragg reflector, and combinations thereof.

The side surface(s) 46 of the elongate disinfection chamber 40 (i.e. the surface(s) perpendicular to the top and bottom surfaces described above) may be formed from or coated with a material that causes total internal reflection (TIR), or attenuated total internal reflection (ATR), where the material is reflective but somewhat absorbing, such that some power is lost when radiation is incident on the ATR material. A TIR material may be preferred in some embodiments for better reflection, but an ATR material may be used for other reasons such as cost, durability, etc. In some embodiments, the elongate disinfection chamber is formed from a durable, inexpensive material such as plastic or polycarbonate, with the interior surface coated with a material that causes TIR or ATR. Examples of suitable coatings and/or materials for forming the disinfection chamber include materials that cause TIR of UV radiation and are not absorbing or substantially not absorbing such as Teflon, Fluorilon 99-U, and any of the materials listed above for coatings for surfaces 48 and 54. The disinfection chamber may be made from, for example, the examples of suitable coatings for the disinfection chamber and/or surfaces 48 and 54 listed above, plastic, metal, glass, or any suitable material.

The optional coatings described above and herein are illustrated in FIG. 7 as element 500.

In some embodiments, one or more surfaces of the disinfection chamber 40 that encounter water, such as the side surfaces or top and bottom surfaces described above may be coated with or otherwise treated with a photocatalytic material such as $TiO_2$. $TiO_2$ may photocatalyze water into OH radicals, which may purify water by breaking down organic material.

In some embodiments, the water disinfection device illustrated in FIG. 7 is used to disinfect fluid in a batch process. For example, the disinfection device may be a water bottle. The top 52 may be removable; for example the top 52 may be a screw-on lid, a clamp-on lid, or a structure secured to the disinfection chamber by any other suitable means. The top 52 may be removed, the disinfection chamber 40 filled with water, and the UV radiation source 50 activated, for example by pressing a button or flipping a switch (not shown in FIG. 7). The UV radiation source 50 may irradiate the water in the disinfection chamber 40 until, for example, automatically switched off or deactivated by a user. The top 52 may then be removed, and the disinfected water removed. In some embodiments, a single UV radiation source 50 may be disposed at the bottom of the water bottle, rather than the top, such that the water to be disinfected is in close enough proximity to the UV radiation source to act as a heat sink to the UV radiation source. In addition, placing UV radiation source 50 at the bottom of a water bottle, rather than the top, may reduce or eliminate losses associated with TIR at an air gap between the UV radiation source and the fluid, which may be caused by incomplete filling of the water bottle.

Figure 8:
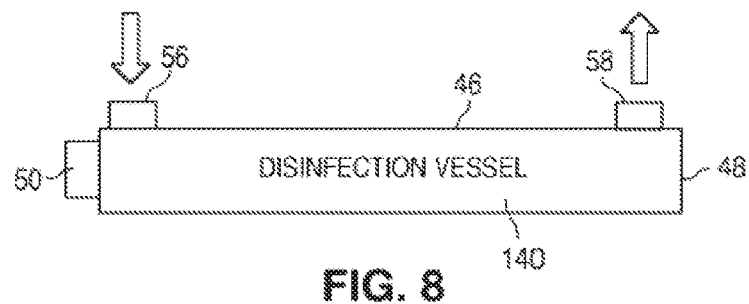
FIG. 8 is a cross sectional view of a continuous-flow UV disinfection system.

FIG. 8 is a cross sectional view of one embodiment of a water disinfection device, which may disinfect water in a continuous-flow process, rather in than a batch process like the device illustrated in FIG. 7. In the device of FIG. 8, the UV radiation source 50 is disposed at one end of the elongate disinfection chamber 140, as in FIG. 7, and irradiates the disinfection chamber 140 when activated. The top and bottom 48 ends of the elongate disinfection chamber 140 may be coated or formed from a UV reflective material, as in FIG. 7. The interior surface(s) 46 of the disinfection chamber 140 may be coated with a TIR or ATR material, as in FIG. 7.

In the device illustrated in FIG. 8, water to be disinfected flows into the disinfection chamber 140 through inlet 56. Water flows through the disinfection chamber 140 toward outlet 58, where the disinfected water flows out of the disinfection chamber 140. The device illustrated in FIG. 8 is not to scale; the disinfection chamber 140 may be much longer and the inlet 56 and outlet 58 spaced much further apart than illustrated in FIG. 8. For example, the disinfection chamber 140 may be at least 10 times longer than it is wide in some embodiments, at least 100 times longer than it is wide in some embodiments, and at least 500 times longer than it is wide in some embodiments. The disinfection chamber 140 is sufficiently long that the water spends enough time in the disinfection chamber to be exposed to sufficient UV radiation to disinfect the water.

Disinfection chamber 140 may be, for example a flexible plastic hose, or any other suitable material. In some embodiments, the inlet 56 (and the UV radiation source 50 in some embodiments) is submersible in a water body, such that a user may suck or pump water toward the outlet 58.

Figure 1:
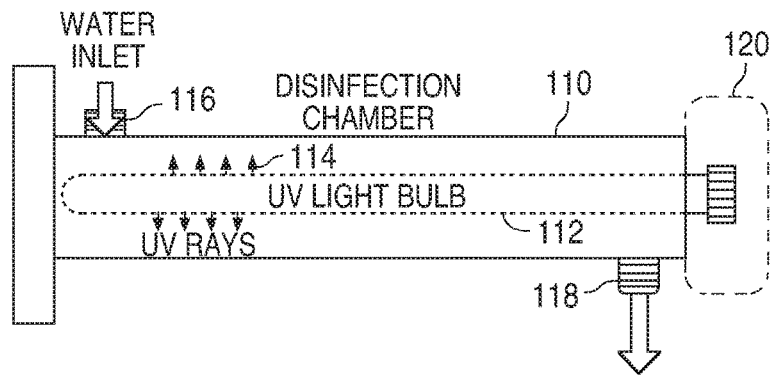
FIG. 1 is a cross sectional view of a prior art UV disinfection system.

Unlike in the device of FIG. 1, where the UV source is disposed within the chamber such that UV radiation is emitted radially, in the device illustrated in FIGS. 7 and 8, the UV source 50 is disposed at one end of the chamber, such that radiation is emitted longitudinally, down the length of the elongate chamber.

Figure 9A:
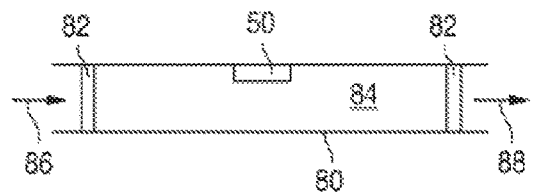
FIG. 9A is a cross sectional view of a continuous-flow UV disinfection system including a fluid permeable structure.

FIG. 9A is a cross sectional view of a continuous-flow disinfection chamber including a fluid-permeable structure such as a filter. In the device of FIG. 9, a disinfection chamber 84 is defined by elongate sidewalls 80, and filters 82 disposed on either end of chamber 84. Fluid enters at 86, flows through filter 82 into the chamber 84, then through a second filter 82, where it exits the chamber at 88. A UV radiation source 50 is disposed on sidewall 80, or at any other appropriate location. As in FIG. 8, the disinfection chamber may be flexible (such as, for example, a plastic tube), or rigid. The disinfection chamber is typically elongate, though it may be any suitable shape.

Figure 9B:
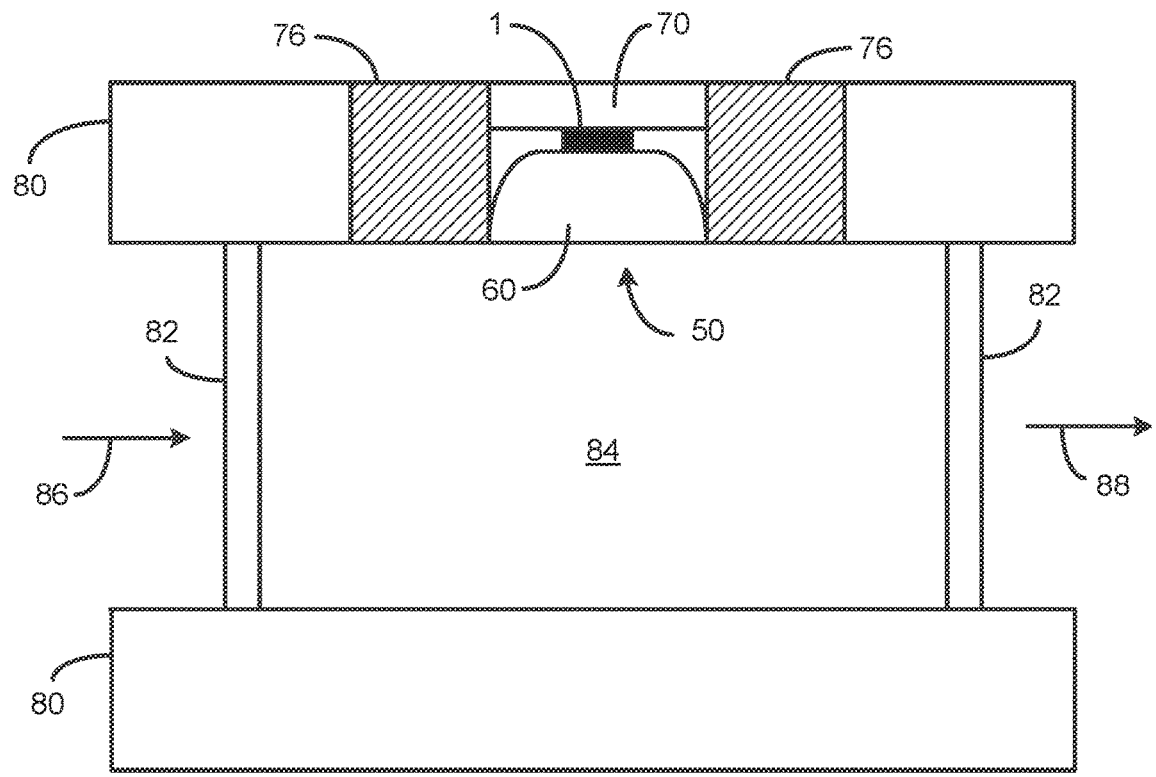
FIG. 9B is a cross sectional view of the system of FIG. 9A showing more detail of the UV radiation source along a sidewall of the chamber and an optic in contact with the fluid.

FIG. 9B is a cross sectional view of the system of FIG. 9A showing more detail of the UV radiation source 50 along a sidewall 80 of the chamber 84. The UV radiation source 50 includes the UVLED 1, mount 70, and an optic 60 in contact with the fluid in the chamber 84. A sealing material 76 (also shown in FIG. 5) may be used to seal the UVLED 1 and optic 60.

Filters 82 may be any suitable structure through which fluid may pass. Filters 82 may filter out some or all particulate matter in the fluid, though this is not required. Filters 82 may also be reflective of UV radiation, such that light emitted by UV radiation source 50 is trapped in chamber 84. Filters 82 may be any suitable material including, for example, porous aluminum, aluminum screens, or Teflon particles sintered into porous Teflon made by Porex, Inc. The length and diameter of chamber 84, the porosity of filters 82, the radiative power emitted by UV radiation source 50, and other characteristics may be selected such that at a predetermined flow rate, the fluid (e.g. air, water, or any other appropriate fluid) spends sufficient time in chamber 84 to disinfect the fluid.

In some embodiments, some or all of the walls of the chamber 84 may be coated with a photocatalytic material, as described above. Since photocatalytic disinfection requires close proximity between the fluid and the photocatalytic material, other structures coated with or formed from a photocatalytic material may be disposed in the chamber 84. In an embodiment including a photocatalytic material, the fluid may be disinfected three ways: mechanical filtering by filters 82, disinfection by UV radiation from UV radiation source 50, and disinfection by OH radicals created by the interaction of the photocatalytic material with UV radiation.

Figure 10:
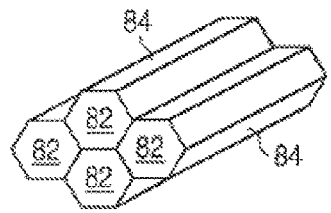
FIG. 10 illustrates multiple continuous-flow UV disinfection chambers in a close-packaged arrangement.

FIG. 10 illustrates multiple disinfection chambers 84, such as the one illustrated in FIG. 9A, in a close-packed arrangement. Disinfection chambers may be added as necessary to reach a desired throughput of fluid. Though the individual disinfection chambers are hexagonal, to maximize the area of the disinfection chambers in cross section, the individual disinfection chambers may be any suitable cross section.

Figure 11:
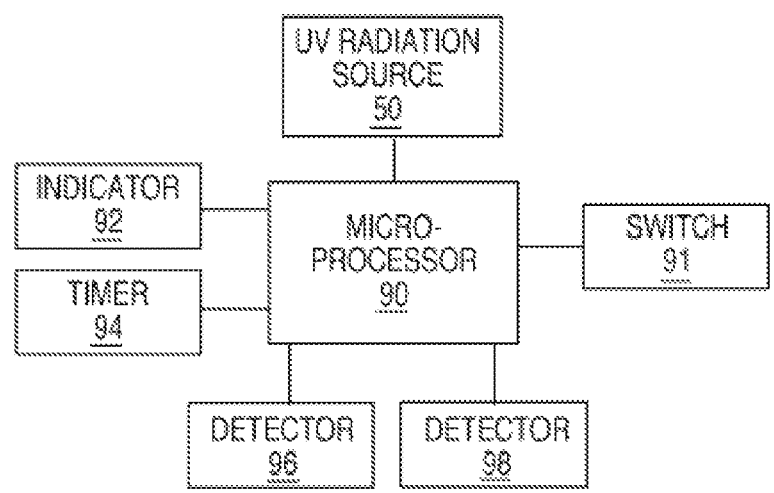
FIG. 11 is a block diagram of a circuit for controlling a UV disinfection system.

FIG. 11 is a block diagram of a circuit, which may control a UV radiation source in any of the disinfection chambers described above. Any suitable circuit may be used. Not all of the components illustrated in FIG. 11 are necessary in all embodiments. The components may be disposed on or in a mount, described above, and electrically connected to each other as illustrated via the mount, a circuit board, or any other suitable structure. UV radiation source 50 may be connected to a microprocessor 90, which may turn the UV radiation source 50 on and off, and may adjust the power to UV radiation source 50. A switch 91, which may be user-activated or automatic, and may be any suitable switch, may activate the UV radiation source directly (not shown in FIG. 11), or may activate the microprocessor, which turns on the UV radiation source.

The amount of time that the fluid is exposed to radiation from UV radiation source may be dictated by a timer 94, which may count a predetermined amount of time, after which the microprocessor 90 may turn off UV radiation source 50. An indicator 92, such as a light or any other suitable indicator, may indicate whether UV radiation source 50 is emitting UV radiation.

A detector 96 may detect an amount of UV radiation at a given point in the disinfection chamber. The amount of UV radiation emitted by source 50 may be adjusted accordingly by microprocessor 90. A second detector 98 may be used to detect whether the UV radiation source 50 is functioning properly. For example, first detector 96 may be positioned near UV radiation source 50, and second detector 98 may be positioned far from UV radiation source 50. When UV radiation source 50 is on, the amount of UV radiation detected by each of detectors 96 and 98 may be compared. If detector 96 indicates a higher amount of UV radiation and detector 98 indicates a lower amount of UV radiation, the fluid may be contaminated with particulate matter. If detectors 96 and 98 both indicate a low amount of UV radiation, the UV radiation source 50 may not be functioning properly. Indicator 92 may be used to indicate to a user that UV radiation source 50 is not functioning properly.

In one operation, a user activates switch 91. In response, microprocessor 90 turns on UV radiation source 50. Microprocessor 90 may also switch indicator 92 to a status indicating the UV radiation source is disinfecting. The amount of UV radiation is measured by detector 96. In response, microprocessor 90 may adjust the amount of time that the UV radiation source 50 stays on, and/or the power to UV radiation source 50, in order to deliver a sufficient dose of UV radiation to disinfect the fluid. Once the dose is reached, microprocessor 92 may switch off UV radiation source 50, and switch off indicator 92 or change indicator 92 to a status indicating the UV radiation source is finished disinfecting.

Having described the invention in detail, those skilled in the art will appreciate that, given the present disclosure, modifications may be made to the invention without departing from the spirit of the inventive concept described herein. In particular, different features and components of the different devices described herein may be used in any of the other devices, or features and components may be omitted from any of the devices. A characteristic of, for example, the optic, described in the context of one embodiment, may be applicable to any embodiment. Suitable materials described for a particular component in a particular embodiment may be used for other components, and/or in other embodiments. Therefore, it is not intended that the scope of the invention be limited to the specific embodiments illustrated and described.

What is being claimed is:

1. A structure comprising:
    an elongated chamber for holding a fluid, the chamber having a sidewall generally parallel with a flow of the fluid through the chamber;
    a ultraviolet light emitting diode (UVLED) disposed along the sidewall of the chamber, the UVLED comprising a semiconductor device comprising an active layer that emits radiation having a peak wavelength in an ultraviolet range disposed between an n-type region and a p-type region; and
    an optic disposed over a major surface of the UVLED such that the optic is in contact with the fluid, wherein the optic comprises a lens.

2. The structure of claim 1 further comprising a mount, wherein the UVLED is attached to the mount.

3. The structure of claim 2 wherein the mount comprises one of ceramic, circuit board, metal-core printed circuit board, and silicon.

4. The structure of claim 2 further comprising a sealing material disposed over the mount and forming a seal that protects the UVLED from the fluid.

5. The structure of claim 4 wherein the sealing material is UV-stable and transparent.

6. The structure of claim 4 wherein the sealing material is a different material from the optic.

7. The structure of claim 2 further comprising a space between the mount and the optic.

8. The structure of claim 7 wherein the space is filled with one of oil and an index matching material.

9. The structure of claim 1 wherein the optic is a solid, transparent material.

10. The structure of claim 1 wherein:
    the optic comprises a first surface proximate the UVLED and a second surface, the second surface comprising an outlet surface opposite the first surface; and
    the outlet surface is matched to a shape of the chamber.

11. The structure of claim 1 wherein the optic is quartz.

12. The structure of claim 1 wherein the optic is one of glass, silicone, and sapphire.

13. The structure of claim 1 wherein the sidewall of the chamber is coated with a reflective coating.

14. The structure of claim 13 wherein the reflective coating comprises a multilayer stack comprising aluminum and $SiO_2$.

15. A structure comprising:
    an elongated chamber for holding a fluid, the chamber having a sidewall generally parallel with a flow of the fluid through the chamber;
    a ultraviolet light emitting diode (UVLED) disposed along the sidewall of the chamber, the UVLED comprising a semiconductor device comprising an active layer that emits radiation having a peak wavelength in an ultraviolet range disposed between an n-type region and a p-type region;
    a sealed compartment positioned on the sidewall of the chamber, wherein the UVLED is disposed within the sealed compartment, the sealed compartment comprising first sidewalls and a lens, wherein the lens is in direct contact with the fluid, and wherein the sealed compartment isolates and protects the UVLED from the fluid.

16. The structure of claim 15 wherein the lens is quartz.

17. The structure of claim 15 wherein the UVLED is attached to a mount.

* * * * *